United States Patent [19]

Ogawa et al.

[11] Patent Number: 4,910,225

[45] Date of Patent: Mar. 20, 1990

[54] LOCALLY ADMINISTRABLE THERAPEUTIC COMPOSITION FOR INFLAMMATORY DISEASE

[75] Inventors: Takahiro Ogawa, Nishinomiya; Yoshikazu Kuribayashi, Kobe; Kazumichi Ushio, Nishinomiya; Akira Ohtori, Nara, all of Japan

[73] Assignees: Senju Pharmaceutical Co., Ltd., Osaka, Japan; A. H. Robins Company, Incorporated, Richmond, Va.

[21] Appl. No.: 301,033

[22] Filed: Jan. 24, 1989

[30] Foreign Application Priority Data

Jan. 27, 1988 [JP] Japan .................................. 63-16683

[51] Int. Cl.$^4$ ........................................... A61K 31/195
[52] U.S. Cl. .................................................... 514/561
[58] Field of Search ........................................ 514/561

[56] References Cited

U.S. PATENT DOCUMENTS

| 4,045,576 | 8/1977 | Welstead et al. | 424/309 |
| 4,126,635 | 11/1978 | Welstead et al. | 562/441 |
| 4,568,695 | 2/1986 | Moran et al. | 514/648 |
| 4,683,242 | 7/1987 | Poser | 514/539 |

FOREIGN PATENT DOCUMENTS

| 0221753 | 5/1987 | European Pat. Off. . |
| 58-201710 | 2/1984 | Japan . |

OTHER PUBLICATIONS

Walsh et al., Journal of Medicinal Chemistry, 1989, vol. 27, No. 11, pp. 1379–1388.
Chem. Abst. 107-(1987)-211870z.

*Primary Examiner*—Stanley J. Friedman
*Attorney, Agent, or Firm*—Wenderoth, Lind & Ponack

[57] ABSTRACT

This invention relates to a locally administrable therapeutic composition for inflammatory disease which is characterized by comprising benzoylphenylacetic acid of the formula

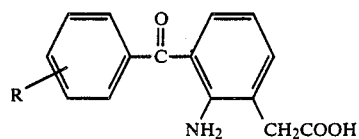

(wherein R is a hydrogen or halogen atom), or a salt thereof, or the hydrate of said acid or salt, as active ingredient.

An ophthalmic composition according to the invention can treat effectively inflammatory eye disease by topical application, is not an irritant to the eye, and has a superior effect to conventional drugs of the same or similar type.

The aqueous composition prepared in accordance with this invention has excellent stability and can be used advantageously as a nasal or otic composition as well as an ophthalmic one in the treatment of inflammatory otic or nasal disease.

9 Claims, No Drawings 4,910,225

LOCALLY ADMINISTRABLE THERAPEUTIC COMPOSITION FOR INFLAMMATORY DISEASE

BACKGROUND OF THE INVENTION

1. Field of the Invention

This invention relates to a locally administrable therapeutic composition for inflammatory eye disease as well as nasal or otic inflammatory disease.

More particularly, it relates to a locally administrable therapeutic composition for inflammatory eye as well as for nasal or otic inflammatory disease, which contains as active ingredient a benzoylphenylacetic acid derivative, a salt thereof or the hydrate of said acid or salt.

The other object of the present invention is to provide a stable locally administrable aqueous composition such as eye drop, otic composition and nasal composition containing the above compounds.

2. Description of the Prior Art

That certain benzoylphenylacetic acid derivatives, when orally administered, exhibit anti-inflammatory activity has been reported in detail in Journal of Medicinal Chemistry, Volume 27, pages 1379-1388 (1984), among others. Furthermore, Japanese Laid Open Patent Publication No. 126124/1987 describes pharmaceutical compositions for percutaneous administration which contain these compounds. However, none of the published literature-inclusive of the above-mentioned patent specification-contains any description indicating or suggesting that these medicinal substances are effective against inflammatory disease of the eye, nose or ear when they are administered topically.

For the treatment, with topical application of drugs, of inflammatory ophthalmopathy such as uveitis and conjunctivitis which are most frequently observed in the ophthalmological field, steroid drugs such as dexamethazone have so far been employed. Topical application of steroid drugs to the eye has some apprehension of increasing intraocular pressure to cause glaucoma. And, there is a fear not only of causing corneal perforation when such steroid drugs are applied to patients suffered from corneal herpes, corneal ulcer or the like, but also of induction of corneal herpes, keratomycosis, Pseudomonas infections and the like by the topical application of steroid drugs. As there has been known such-effects as above, steroid anti-inflammatory agents shall be applied with particular care. In spite of such a situation, there has not been known any non-steroid anti-inflammatory agent compatible with steroid anti-inflammatory drugs in effectiveness for the treatment of inflammatory opthalmopathy such as uveitis. Thus, in the present stage in this technical field, for the treatment of inflammatory ophthalmopathy, it is hardly possible not to use steroid anti-inflammatory agents with particular care to avoid the side effects as above-mentioned. Under such circumstances, it is natural that ophthalmological experts are awaiting the appearance of non-steroid drugs which are effectively usable against uveitis or the like.

The present inventors investigated to find out topically applicable drugs with lesser side-effects and with superior effectiveness by which topically applicable drugs having been employed in the treatment of inflammatory ophthalmopathy, i.e. steroid anti-inflammatory agent, can be replaced. As a result, the present inventors unexpectedly found that certain derivatives of benzoylphenylacetic acid are very effective in the treatment of inflammatory ophthalmopathy, especially of uveitis, by topical application, and that the effectiveness of such drugs is compatible with that of conventional steroid anti-inflammatory drugs.

Furthermore, since the inventors obtained the finding that there are some problems that the above-mentioned benzoylphenylacetic acid derivatives are unstable in an aqueous solution with the optimal pH range for a locally administrable therapeutic composition, they extensively investigated in search of the method for the preparation of a stable aqueous solution. As a result, we have succeeded in preparing a stable aqueous composition. Thus, the stable aqueous composition according to the invention are achieved based on the above finding.

While a number of non-steroid compounds fall under the category of anti-inflammatory agents, all of them are not effective in treating inflammatory eye diseases when topically administered to the eye. This is because there are several problems lying before them. First, when topically administered to the eye, a medicinal agent has to pass through the cornea so that it can reach the site of inflammation. Even when it has succeeded in arriving at the site of inflammation, it must remain there in a necessary concentration for a necessary period of time. If it fails to meet these requirements, it will be unable to produce expected therapeutic effects. Furthermore, in case it is irritative to the eye, it is rather possible that the topical administration of the medicinal agent to the eye would cause exacerbation of symptoms. Therefore, great caution and much care are necessary in selecting a medicinal agent for topical administration to the eye. Furthermore, in case of administration in the form of eye drops, it goes without saying that it is desirable that the eye drop is stable for a long period of time in an aqueous solution without decomposition or forming insoluble matters.

Accordingly, it is an object of the invention to solve the above problems and provide a novel and useful agent for ophthalmic use.

Moreover, the other object of the invention is to provide a sufficiently stable aqueous solution such as eye drops, otic solution and nasal solution which contains the above compounds when stored for a long period of time.

SUMMARY OF THE INVENTION

The present invention, which has been completed based on the above finding, provides a therapeutic composition for administration to the eye for the treatment of inflammatory eye diseases which contains as active ingredient a benzoylphenylacetic acid of the formula

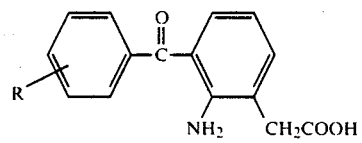

[wherein R is a hydrogen or halogen atom], or salt thereof, or the hydrate of said acid or salt. In the formula, the halogen atom represented by R is, for example, fluorine, chlorine, bromine or iodine. The above compound to be used in accordance with the invention may be in a salt form. The salt includes alkali metal salts such as sodium salt and potassium salt, alkaline earth metal salts such as calcium salt and magnesium salt, among others, and any salt may suitably be used provided that it can attain the object of the invention. The compounds defined above may be obtained in the form of a hydrate depending on the conditions of synthesis, recrystallization and so forth, and such form may be used in practicing the invention without any inconvenience or trouble.

Further, the above compounds may be unstable when stored in an aqueous solution for a long period of time, and there are some problems in the stability of an aqueous solution containing the compounds. Therefore the inventors extensively investigated the stabilizing method in order to enhance the stability. As a result, unexpectedly, they have succeeded in stabilizing the solution by incorporating a water-soluble polymer and sulfite and adjusting the pH to about 6-9.

DETAILED DESCRIPTION OF THE INVENTION

The compounds to be used as active ingredients in the topically administrable therapeutic compositions for inflammatory eye disease as well as nasal or otic disease in accordance with the invention (although such compositions are occasionally hereinafter referred to as "opthalmic composition according to the present invention", use of this abbreviation does not exclude the application of the composition in the nasal or otic fields) can be produced as described in the above-cited report in Journal of Medicinal Chemistry, Volume 27, pages 1379-1388 (1984) or U.S. Pat. No. 4,045,576, for instance, or by a modification of the method described therein. The ophthalmic compositions according to the invention can be prepared in the form of eye drops, eye ointments and so on in the same manner as various known compositions for topical administration to the eye. Thus, a compound of the above formula or a mixture of two or more compounds of the above formula is preferably made up into an aqueous or non-aqueous solution or mixed with an ointment base suited for ophthalmic use. On that occasion, an aqueous base generally used in the production of ophthalmic preparations, for example sterile distilled water, is suitably used as the aqueous base and the pH thereof is adjusted to a level suited for topical administration to the eye. It is desirable that an appropriate buffer should be added in adjusting the pH. The pH of the ophthalmic compositions according to the invention is selected with due consideration paid to the stability and topical eye irritativity of the active ingredient, among others. According to the present invention, the stability of an aqueous composition containing the above compounds is remarkably enhanced by incorporating a water-soluble polymer and sulfite, and adjusting the pH to 6.0-9.0, preferably about 7.5-8.5. The eye irritation of the solution is not observed. A water-soluble polymer includes polyvinyl pyrrolidone, carboxypropylcellulose, hydroxyethylcellulose, hydroxypropylcellulose, polyvinyl alcohol, sodium salt of polyacrylic acid an so on. Polyvinyl pyrrolidone is preferred among them. The concentration of a water-soluble polymer is in the range of about 0.1 to 10 w/w%. Sulfite includes sodium, potassium, magnesium, calcium salt and so on. The concentration of sulfite is in the range of about 0.1 to 1.0 w/w %. The pH adjustment is generally conducted with sodium hydroxide or hydrochloric acid, for instance, and it is advisable to form a buffer solution by combined use of, for example, sodium acetate, sodium borate or sodium phosphate and acetic acid, boric acid or phosphoric acid, respectively. The ophthalmic compositions according to the invention may further contain pharmaceutically active ingredients, such as an anti-inflammatory agent of another kind, an analgesic and an antimicrobial, unless they are unfit for the purpose of attaining the object of the invention. Examples of such antiinflammatory agent are indomethacin and pranoprofen. Usable examples of the antimicrobial agents are penicillins, cephalosporins, and synthetic antimicrobial agents of the quinolonecarboxylic acid series. Among these active ingredients for combined use with the active ingredient according to the invention, the anti-inflammatory agent is expected to be synergistic with said active ingredient in the ophthalmic compositions according to the invention. The analgestic is suited for the purpose of alleviating inflammation-associated pain, and the antimicrobial agent is suited for the purpose of preventing secondary infection. It is of course possible to incorporate active agents other than those mentioned above in the ophthalmic compositions according to the invention unless the object of the invention cannot be attained due to the presence thereof.

In preparing the ophthalmic compositions according to the invention as mentioned above, an isotonizing agent, a microbicidal agent or preservative, a chelating agent, a thickening agent and so forth may be added to the compositions in accordance with the general practice of ophthalmic preparation manufacture. The isotonizing agent includes, among others, sorbitol, glycerine, polyethylene glycol, propylene glycol, glucose and sodium chloride. The preservative includes para-oxybenzoic acid esters, benzyl alcohol, parachloro-meta-xylenol, chlorocresol, phenetyl alcohol, sorbic acid and salts thereof, thimerosal, chlorobutanol, and the like. The chelating agent is, for example, sodium edetate, sodium citrate or sodium salt of condensed phosphoric acid. In preparing the ophthalmic compositions according to the invention in the form of eye ointments, the ointment base can be selected from among petrolatum, Macrogol, carboxymethylcellulose sodium, etc.

The ophthalmic composition according to this invention is prepared by incorporating the active compound in a base or vehicle for topical application to the eye. To prepare a liquid preparation, the concentration of the active ingredient may range from about 0.001% to about 10% and is preferably in the range of about 0.01% to about 5%. An ointment may be prepared by using the active compound in a concentration from about 0.001% to about 10%, preferably about 0.01% to about 5%. The ophthalmic composition of this invention may be administered in accordance with the following schedules. In the form of eye-drops, one to several drops per dose are instilled with a frequency of once to 4 times a day according to the clinical condition. Of course, the dosage may be adjusted according to symptoms. The ophthalmic composition according to this invention can be used topically for the treatment of inflammatory diseases of the eye without causing local irritant effects and produces beneficial effects surpassing those obtainable with the conventional drugs of the same type.

According to this invention, there can be obtained a stable aqueous composition such as otic composition or nasal composition. Other conventional methods can be used unless unsuitable for the object of this invention. Among others, an isotonizing agent, buffer solution and preservatives can be used. The concentrations of the compounds of the invention varies depending on symptoms and so on, and usually may be in the range of about 0.001 to about 10%, preferably about 0.01 to about 5%.

The following experimental examples are given to delineate the efficacy profile of the ophthalmic composition of this invention and the stability of the aqueous compositions of the invention.

EXPERIMENTAL EXAMPLE 1

Anti-inflammatory effect of the ophthalmic agent according to this invention in experimental ophthalmitis induced by bovine serum albumin in white rabbits

[Animals]

Seventeen male white rabbits weighing about 2 kg were used. They were fed with 80 g of Labo RG-RO (Nippon Agricultural Co., Ltd.) daily and had free access to tap water.

[Test drug]

Sodium 3-(4-bromobenzoyl)-2-aminophenylacetate monohydrate (hereafter referred to as Compound [I] was used as 0.5% and 0.1% ophthalmic solutions. These ophthalmic solutions had a pH value of 8.11 and osmolarities of 310 mOsm/kg·$H_2O$ and 325 mOsm/kg·$H_2O$, respectively. Bovine serum albumin (hereafter referred to as "BSA") was dissolved in physiological saline to a concentration of 5% and sterilized by filtration. A 0.1 ml portion of the solution was injected into the central part of the vitreus of both eyes using a 27G needle under anesthesia with 0.4% oxybuprocaine hydrochloride to induce ophthalmitis (ophthalmitis I). After 28 days when ophthalmitis I had nearly recovered, 2.5% BSA solution was administered in a dose of 25 mg/ml/kg into the auricular vein to cause ophthalmitis (ophthalmitis II). The severity of ophthalmitis was rated according to the rating scale[1] of Yamauchi et al., based on the Draize method in which an increased weight given to the internal segment of the eye. Observation was made with a frequency of once in one or two days during the peak period of inflammation and once in three or four days before and after the peak period for ophthalmitis I and 3, 6, 12 and 24 hours after intravenous injection of BSA for ophthalmitis II.

[1] Hideyasu Yamauchi, Makoto Ingu, Tadashi Iso and Kozo Uda: Anti-inflammatory effect of fluorometholone ophthalmic solution in experimental uveitis in rabbits, Folia Ophthalmologica Japonica, 24: 969–79 (1973).

[Results]

Anti-inflammatory effect in ophthalmitis I

Table 1 shows the sum of scores for respective parameters during a peak inflammatory period of 3 days after aseptic injection of 5% BSA into the central part of the vitreous.

Table 2 shows the amount of protein, white blood cell count and the concentration of prostaglandins in the anterior chamber aqueous humor.

Anti-inflammatory effect in ophthalmitis II

The administration of 2.5 ml/kg of 2.5% BSA solution into the auricular vein after 29 days when the inflammatory symptoms of ophthalmitis I had substantially subsided resulted in a relapse of inflammation after 3 hours in the physiological saline group, where both the external and internal segment of the eye after 12 hours showed inflammatory pictures similar to those observed at the peak of ophthalmitis I. These symptoms were still observed even after 24 hours. Table 3 shows the scores for respective parameters at 3, 6, 12 and 24 hours after the intraveous injection of BSA. Table 4 shows the amount of protein, white blood cell count and the concentration of prostaglandins in the anterior chamber aqueous humor.

Administration of the test drug

Gross observation was made on the day after injection of BSA into the vitreous body and with the animals arranged in the decreasing order of severity of ocular inflammation, grouping was carried out in such a manner that the intensity distribution would be uniform over the groups. Thus, a physiological saline group of 7 animals, a 0.1% Compound [I] instillation group of 4 animals and a 0.5% Compound [I] instillation group of 5 animals were provided. After this grouping procedure, the test drugs and saline were respectively instilled into both eyes of the rabbits, 50 μl per dose, 4 times a day. For induction of ophthalmitis II, each drug was instilled into both eyes, 50 μl per dose, immediately after injection of BSA into the auricular vein and at 1-hour intervals thereafter, for a total of 14 times.

Evaluation of results

In ophthalmitis I, Compound [I] at concentrations of 0.1% and 0.5% caused a potent and dose-dependent inhibition for both the external and the internal segment of the eye. Furthermore, at both concentration levels, Compound [I] produced a substantially complete inhibition of prostaglandins in the aqueous humor in ophthalmitis I.

In regard to the inhibitory effect on inflammatory symptoms, as evaluated by gross observation, which are induced by the intraveous injection of antigen, the Compound [I] according to this invention produced a substantially complete inhibition at both concentrations. As to white blood cell count, all drugs produced nearly the same degree of inhibition in both the internal and the external segments of the eye.

For any of the drugs, no body weight suppression was observed even after 28 consecutive days of treatment. In the organs including the thymus, spleen, adrenal and so on, anatomically no abnormality was found.

EXPERIMENTAL EXAMPLE 2

The effect of the compounds according to this invention on carrageenin edema in rats Test drugs 1. Sodium 3-(4-bromobenzoyl)-2-aminophenyl-acetate (hereinafter referred to as Compound [I])
2. Sodium 3-(4-chlorobenzoyl)-2-aminophenyl-acetate (hereinafter referred to as Compound [II])
3. Sodium 3-benzoyl-2-aminophenylacetate (hereinafter referred to as Compound [III])

Method

Using female Wister rates weighing 100 g in groups of 5 animals or 10 eyes, 0.05 ml of 1% carrageenin (dissolved in physiological saline at 50° C.) as a phlogogen was injected beneath the conjuctiva of both eyes to induce edema. Physiological saline, as a control, and test drugs were respectively instilled into both eyes 40 and 20 minutes before and immediately after the injection of carrageenin, in the amount of 2.5 μl per dose. Four hours after the phlogogen treatment, each animal was sacrificed by cervical dislocation and in accordance with the method of Maistrello et al.[2], the scalp was peeled off toward the eyelid and the edematous portion together with the skin was removed along the lid margin and weighed. The degrees of inhibition of carrageenin edema in the control group and drug treatment group are shown in Table 5. Each drug group showed a significant difference from the control group, indicating the effectiveness of the three compounds against acute ocular inflammation.

[2] Maistrello et al.: Quantitative Effect of Topically Applied Anti-inflammatory Agents on External Ocular Inflammation in Rats: Journal of Pharmaceutical Science, volume 62, pp. 1455–60(1973).

EXPERIMENTAL EXAMPLE 3

Effects on atropine-resistant miosis and on protein increase after paracentesis

The experiment was divided into two parts, i.e. Experiment 3.a, in which the effect of Compound [I] was evaluated, and Experiment 3.b, in which indomethacin, the most known anti-inflammatory drug with strong cyclooxgenase inhibitory activity, was evaluated.

[Test drugs]

The solutions of the following formulas were used.

| a. Compound [I] | | | | |
|---|---|---|---|---|
| Compound [I] | 0.1 | 0.01 | 0.001 | 0.0001% |
| Boric acid | 1.0 | 1.0 | 1.0 | 1.0% |
| Borax | q.s. | q.s. | q.s. | q.s. |
| Sodium chloride | 0.25 | 0.25 | 0.25 | 0.25% |
| Sodium edetate | 0.02 | 0.02 | 0.02 | 0.02% |
| Benzalkonium chloride | 0.005 | 0.005 | 0.005 | 0.005% |
| Tween 80 | 0.3 | 0.3 | 0.3 | 0.3% |
| (pH 8.0, Osmotic pressure 310 mOsm/Kg.$H_2O$) | | | | |
| b. Indomethacin | | | | |
| Indomethacin | | 0.5% | | |
| Castor oil | | q.s. | | |

[Animals]

Totally 28 male albino rabbits (4 rabbits×7 groups) with a body weight of about 2 kg werr used. They had been confirmed, before the experiment, to have mydriatic response to 1% atropine for at least 4 hours.

[Test procedure]

50 μl each of 1% atropine solution was instilled into both eyes of the animals one hour before the 1st paracenthesis, in which approx. 0.2 ml/eye of aqueous humor (primary aqueous humor) was collected. Topical application of 50 μl each of the test drug solutions was conducted 30 min before the paracenthesis. Pupil diameter of each eye was measured with a slide caliper immediately before and 10 min after the paracenthesis. The 2nd paracenthesis was conducted 90 min after the 1st one, in which approx. 0.2 ml/eye of aqueous humor (secondary aqueous humor) was collected.

[Results]

As shown in Table 6, Compound [I] exhibited a dose-related inhibitory activity on miosis after paracentesis at the concentrations of 0.0001–0.1%, whereas little effect was observed with indomethacin at the concentrations as high as 0.5%. As shown in Table 7, Compound [I] exhibited a strong and dose-related inhibitory activity on protein increase after paracenthesis, in which the effect of 0.01% of Compound [I] was equivalent to that of 0.5% indomethacin. It is well known that atropine-resistant miosis and protein increase in aqueous humor after paracenthesis are caused by prostaglandin $E_2$, which is one of the most important chemical mediators of inflammation and is synthesized immediately after mechanical injury. The results, therefore, indicate that Compound [I] has stronger anti-inflammatory effect than indomethacin.

EXPERIMENTAL EXAMPLE 4

| Formula | |
|---|---|
| Compound [I] | 0.1 g |
| Borax | 1.0 g |
| Sodium borate | Sufficient quantity |
| Sodium chloride | 0.25 g |
| Disodium edetate | 0.02 g |
| Benzalkonium chloride | 0.005 g |
| Polysorbate 80 | 0.3 g |
| Sterile purified water | To make 100 ml |

Stability was observed at 60° C. of the compound by changing pH (6.0, 7.0, 8.0 and 9.0) of the above formula. The results are shown in Table 8.

Of the above four, the formula at the pH of 8 is most stable. In the formula, the change in residue rate were not almost observed but in three weeks red insoluble matters were observed.

EXPERIMENTAL EXAMPLE 5

As a result of extensive examination on preventing the red insoluble matters, the stability was observed by incorporating polyvinyl pyrrolidone.

| Formulas | B-1 | B-2 |
|---|---|---|
| Compound [I] | 0.1 g | 0.1 g |
| Boric acid | 1.5 g | 1.5 g |
| Borax | Sufficient quantity | |
| Disodium edetate | 0.02 g | 0.02 g |
| Benzalkonium chloride | 0.007 g | 0.007 g |
| Polysorbate 80 | 0.15 g | 0.15 g |
| Polyvinyl pyrrolidone | 2.0 g | — |
| Sterile purified water | To make 100 ml | |
| | pH 8 | pH 8 |

In the above formulas, the results of the stability at 60° C. are as follows (Table 9):

It was found that by incorporating polyvinyl pyrrolidone, the appearance of red insoluble matters was considerably prevented. In four weeks, however, some insoluble matters were observed.

EXPERIMENTAL EXAMPLE 6

Moreover, as a result of searching for more stable solutions, the inventors obtained the finding that by further incoporating sodium sulfite other than polyvinyl pyrrolidone, the stability was remarkably increased.

| Formulas | B | B-3 |
|---|---|---|
| Compound [I] | 0.1 g | 0.1 g |
| Boric acid | 1.5 g | 1.5 g |
| Borax | Sufficient quantity | |
| Disodium edetate | 0.02 g | 0.02 g |
| Benzalkonium chloride | 0.007 g | 0.007 g |
| Polyvinyl pyrrolidone | 0.15 g | 0.15 g |
| Sodium sulfite | — | 0.2 g |
| Sterile purified water | To make 100 ml | |
| | pH 8 | pH 8 |

As shown in Table 10, the change of appearance was observed in the formula in which sodium sulfite was not incorporated, and the residue increased by about 7%. By contrast, In the solution containing Compound [I] in which polyvinyl pyrrolidone and sodium sulfite coexist, the change of appearance was not observed at all and the decomposition of Compound [I] was not observed either. It was found that the stability was remarkably enhanced. Thus, there can be successfully obtained a stable aqueous composition containing the compounds.

The following are explanatory examples of the ophthalmic composition and other stable aqueous compositions according to the invention.

EXAMPLE 1

| | |
|---|---|
| Sodium 3-(4-Bromobenzoyl)-2-aminophenyl-acetate monohydrate | 0.1% |
| Boric acid | 1.0% |
| Borax | Sufficient quantity |
| Sodium chloride | 0.25% |
| Sodium edetate | 0.02% |
| Benzalkonium chloride | 0.005% |
| Polysorbate 80 | 0.3% |
| Purified water | Sufficient quantity |

The above ingredients are made up into an ophthalmic solution (the total volume being 100 ml) and pH is adjusted to 8.0.

EXAMPLE 2

| | |
|---|---|
| Sodium 3-benzoyl-2-amino-phenyl-acetate | 0.1% |
| Boric acid | 1.0% |
| Borax | 0.02% |
| Sodium chloride | 0.25% |
| Sodium edetate | Sufficient quantity |
| Benzalkonium chloride | 0.005% |
| Polysorbate 80 | 0.3% |
| Purified water | Sufficient quantity |

The above ingredients are made up into an ophthalmic solution (the total volume being 100 ml) and pH is adjusted to 8.0.

EXAMPLE 3

| | |
|---|---|
| Sodium 3-(4-chlorobenzoyl)-2-amino-phenylacetate | 1.0% |
| White petrolatum | Sufficient quantity |

The above ingredients are mixed up into an eye ointment (100 g) in the conventional manner.

EXAMPLE 4

| | |
|---|---|
| Sodium 3-(4-chlorobenzoyl)-2-amino-phenylacetate monohydrate | 0.01 g |
| Carboxymethylcellulose | Sufficient quantity |

The above ingredients are mixed up in the conventional manner to give 100 g of an eye ointment.

EXAMPLE 5

| | |
|---|---|
| Sodium 3-(4-chlorobenzoyl)-2-amino-phenylacetate monohydrate | 1.0 g |
| Sodium chloride | 0.8 g |
| Tween 80 | 0.2 g |
| Purified water | Sufficient quantity |

The above ingredients are made up into an ophthalmic solution (the total volume being 100 ml) and the pH is adjusted to 7.5 with hydrochloric acid.

EXAMPLE 6

Ophthalmic Solution

| | |
|---|---|
| Sodium 3-(4-bromobenzoyl)-2-aminophenyl-acetate monohydrate | 0.1 g |
| Boric acid | 1.25 g |
| Borax | 1.0 g |
| Disodium edetate | 0.02 g |
| Benzalkonium chloride | 0.005 g |
| Polysorbate 80 | 0.15 g |
| Polyvinyl pyrrolidone | 2.0 g |
| Sodium sulfite | 0.2 g |
| Sterile purified water pH 8 | To make 100 ml |

EXAMPLE 7

Ophthalmic Solution

| | |
|---|---|
| Sodium 3-(4-bromobenzoyl)-2-aminophenyl-acetate monohydrate | 0.1 g |
| Boric acid | 0.7 g |
| Borax | Sufficient quantity |
| Sodium chloride | 0.5 g |
| Polysorbate 80 | 0.15 g |
| Methylparaben | 0.013 g |
| Ethylparaben | 0.007 g |
| Polyvinyl pyrrolidone | 2.0 g |
| Sodium sulfite | 0.2 g |
| Sodium edetate | 0.02 g |
| Sterile purified water | To make 100 ml |

EXAMPLE 8

Ophthalmic Solution

| | |
|---|---|
| Sodium 3-(4-bromobenzoyl)-2-aminophenyl-acetate monohydrate | 0.1 g |
| Boric acid | 1.5 g |
| Borax | Sufficient quantity |
| Benzalkonium chloride | 0.005 g |
| Polysorbate 80 | 0.15 g |
| Polyvinyl pyrrolidone | 2.0 g |
| Sodium sulfite | 0.1 g |
| Sterile purified water pH 8 | To make 100 ml |

The following (Table 11) are the residue and appearance of the compositions in Examples 6–8 after 4 weeks at 60° C.

As shown in Table 11, it was found that changes in appearances of the compositions were not observed at all, and the decomposition of the compound was not almost observed, the aqueous compositions being stable, excellent for a long period of time.

EXAMPLE 9

Ophthalmic Solution

| | |
|---|---|
| Sodium 3-(4-bromobenzoyl)-2-aminophenyl-acetate monohydrate | 0.1 g |
| Sodium monohydrogen phosphate | 0.2 g |
| Sodium dihydrogen phosphate | Sufficient quantity |
| Sodium chloride | 0.8 g |
| Benzalkonium chloride | 0.007 g |
| Polysorbate 80 | 0.15 g |
| Polyvinyl alcohol | 1.0 g |

| | |
|---|---|
| Potassium sulfite | 0.2 g |
| Sterile purified water | To make 100 ml |
| pH 8 | |

EXAMPLE 10

Nasal and Otic Solution

| | |
|---|---|
| Sodium 3-(4-bromobenzoyl)-2-aminophenyl-acetate monohydrate | 0.1 g |
| Boric acid | 0.1 g |
| Borax | Sufficient quantity |
| Sodium chloride | 0.8 g |
| Methylparaben | 0.3 g |
| Ethylparaben | 0.1 g |
| Polyvinyl pyrrolidone | 2.0 g |
| Sodium sulfite | 0.1 g |
| Sterile purified water | To make 100 ml |
| pH 7.5 | |

TABLE 1

| | Test Drug | | |
|---|---|---|---|
| Parameter | Physiological saline (14)[a] | Compound [I] 0.1% (8)[a] | Compound [I] 0.5% (10)[a] |
| External Segment | | | |
| Corneal opacity | 2.5 ± 0.5 | 1.0 ± 0.4 (60.0)[b] | 0.4 ± 0.2 *2(48.0)[b] |
| Palpebral cunjunctival injection | 3.8 ± 0.5 | 1.3 ± 0.2 *2(65.8)[b] | 1.5 ± 0.3 *2(36.8)[b] |
| Palpebral conjunctival edema | 0.7 ± 0.3 | 0.1 ± 0.1 (85.7)[b] | 0 *2(100)[b] |
| Balbar conjunctival injection | 6.5 ± 0.7 | 4.5 ± 0.6 (30.8)[b] | 1.6 ± 0.2 *1(74.5)[b] |
| Discharge | 0.3 ± 0.1 | 0 *1 (100)[b] | 0 *3(100)[b] |
| Total Score | 13.7 ± 1.9 | 6.8 ± 1.0 *1(50.4)[b] | 3.5 ± 0.4 *3(74.5)[b] |
| Internal Segment | | | |
| Anterior chamber opacity | 3.0 ± 0.3 | 3.6 ± 0.8 (−20.0)[b] | 2.0 ± 0.4 (33.3)[b] |
| Iridic injection | 6.1 ± 0.6 | 2.6 ± 0.2 *3(57.4)[b] | 1.8 ± 0.2 *3(70.5)[b] |
| Morphological change of iris | 4.4 ± 0.2 | 2.9 ± 0.4 *2(34.1)[b] | 2.9 ± 0.4 *2(34.1)[b] |
| Total Score | 13.5 ± 0.8 | 9.1 ± 1.0 *2(32.6)[b] | 6.6 ± 0.8 *3(51.1)[b] |
| External + Internal | | | |
| Grand Total Score | 27.3 ± 2.5 | 15.9 ± 1.8 *2(41.8)[b] | 10.1 ± 1.0 *3(63.0)[b] |

[Notes to Table 1]
Each value represents the mean ± standard error. The figure in parentheses[a] represents the number of cases, and the figure in parentheses[b] represents the degree (%) of inhibition relative to the physiological saline group. Significant differences from the physiological saline group at the levels of *1 = $p < 0.05$, *2 = $p < 0.01$ and *3 = $p < 0.001$.

TABLE 2

| Drug | Concentration % | Number of Cases | Protein mg/Mml | White Blood Cell Cells/mm³ | Prostaglandin ng/ml |
|---|---|---|---|---|---|
| Physiological saline | — | 7 | 50.3 ± 7.3 | 5869 ± 2194 | 1.89 ± 0.75 |
| Compound [I] | 0.1 | 4 | 48.7 ± 3.8 | 5593 ± 3436 | <0.4[a] |
| | 0.5 | 5 | 28.4 ± 1.6*1 | 1980 ± 654 | <0.4[a] |

[Notes to Table 2]
Each value represents the mean ± standard error; [a]means that the concentration is less than the assay limit (0.4 ng/ml); *1means a significant difference from the physiological saline group at $p < 0.05$.

TABLE 3

| | Test Drug | | |
|---|---|---|---|
| Parameter | Physiological saline (14)[a] | Compound [I] 0.1% (8)[a] | Compound [I] 0.5% (10)[a] |
| 1/10 External Segment | | | |
| Corneal opacity | 1.4 ± 0.3 | 0.6 ± 0.2 (57.1)[b] | 0.6 ± 0.2 (57.1)[b] |
| Palpebral conjunctival injection | 5.7 ± 0.7 | 4.0 ± 0.3 (29.8)[b] | 3.7 ± 0.1 *1(60.5)[b] |
| Palpebral conjunctival edema | 2.0 ± 0.8 | 1.1 ± 0.4 (45.0)[b] | 0.9 ± 0.2 (55.0)[b] |
| Balbar conjunctival injection | 11.1 ± 0.6 | 8.1 ± 0.4 (27.0)[b] | 8.1 ± 0.3 *2(27.0)[b] |
| Discharge | 0.3 ± 0.1 | 0 (100)[b] | 0 (100)[b] |
| Total Score | 20.5 ± 2.5 | 13.1 ± 1.1 *1(32.7)[b] | 13.3 ± 0.6 *1(31.4)[b] |
| Internal Segment | | | |
| Anterior chamber opacity | 1.9 ± 0.3 | 2.8 ± 0.8 (−47.4)[b] | 2.8 ± 0.5 (−47.4)[b] |
| Iridic injection | 7.3 ± 0.8 | 2.8 ± 0.1 *2(61.6)[b] | 3.3 ± 0.3 *2(54.8)[b] |
| Morphological change of iris | 4.3 ± 0.5 | 2.4 ± 0.4 *2(44.2)[b] | 2.9 ± 0.3 *1(32.6)[b] |
| Total Score | 13.5 ± 1.1 | 8.0 ± 1.2 *2(40.7)[b] | 9.0 ± 0.7 *2(33.3)[b] |
| External + Internal | | | |

TABLE 3-continued

| | Test Drug | | |
|---|---|---|---|
| Parameter | Physiological saline (14)[a] | Compound [I] 0.1% (8)[a] | Compound [I] 0.5% (10)[a] |
| Grand Total Score | 33.9 ± 3.5 | 21.8 ± 2.1 *1(35.7)[b] | 22.3 ± 1.1 *1(34.2)[b] |

[Notes to Table 3]
Each value represenets the mean ± standard error. The figure in parentheses [a] represents the number of cases, and the figure in parentheses [b] represents the degree (%) of inhibition relative to the physiological saline group. Significant differences from the physiological saline group at the levels of *1 = p < 0.05, and *2 = p < 0.01.

TABLE 4

| Drug | Concentration % | Number of Cases | Protein mg/Mml | White Blood Cell Cells/mm$^3$ | Prostaglandin ng/ml |
|---|---|---|---|---|---|
| Physiological saline | — | 10 | 39.5 ± 2.20 | 2416 ± 478 | 15.79 ± 4.86 |
| Compound [I] | 0.1 | 8 | 48.7 ± 3.8 | 1489 ± 499 | <0.4[a] *1 |
| | 0.5 | 10 | 28.4 ± 1.6*1 | 1673 ± 277 | <0.4[a] *2 |

[Notes to Table 4]
Each value represents the mean ± standard error; [a] means that the concentration is less than the assay limit (0.4 ng/ml); *1 means a significant difference from the physiological saline group at the level of *1 = p <0.05, and *2 = p <0.01.

TABLE 5

| Compound | Concentration (%) | Weight of Edema* (mg) | Degree of inhibition (%) |
|---|---|---|---|
| Compound [I] | 1.0 | 43.93 ± 4.138 | 16.9** |
| | 2.5 | 36.323 ± 3.308 | 31.3** |
| Compound [III] | 1.0 | 30.98 ± 3.194 | 41.4** |
| | 5.0 | 32.80 ± 2.409 | 37.9** |
| Control | — | 52.17 ± 2.401 | — |
| Compound [II] | 0.5 | 37.52 ± 2.423 | 36.9** |
| | 1.0 | 39.02 ± 3.057 | 34.4** |
| Control | — | 59.47 ± 3.057 | — |

[Notes to Table 5]
*Each value represents the mean ± standard error for 10 eyes.
**Significant differences from the control group at p<0.001.

TABLE 6

| Test drug | Content (%) | Miosis (%) | Inhibition (%) |
|---|---|---|---|
| Physiological saline | — | 23.7 ± 1.94 | — |
| Exp. 3, a | 0.1 | 17.4 ± 3.80 | 24.9 ± 16.4 |
| | 0.01 | 15.4 ± 1.60 *2 | 35.2 ± 6.75 |
| | 0.001 | 19.0 ± 1.44 | 19.7 ± 6.08 |
| | 0.0001 | 21.5 ± 1.97 | 9.2 ± 8.33 |
| Physiological saline | — | 17.6 ± 1.88 | — |
| Indomethicin | 0.5 | 16.4 ± 3.86 | 6.0 ± 21.4 | t-test *2: P < 0.01

Table 7

| Test drug | Content (%) | Primary aqueous humor Protein (μg/ml) | Secondary aqueous humor Protein (μg/ml) | Inhibition (%) |
|---|---|---|---|---|
| Physiological saline | | 0.89 ± 0.20 | 25.04 ± 4.12 | —M |
| Exp. 3, b | 0.1 | 0.76 ± 0.20 | 3.06 ± 0.46 *2 | 87.8 |
| | 0.01 | 0.39 ± 0.04 *1 | 9.29 ± 7.30 *2 | 62.9 |
| | 0.001 | 0.38 ± 0.02 *1 | 18.45 ± 3.53 | 26.3 |
| | 0.0001 | 0.44 ± 0.06 | 23.45 ± 1.67 | 6.3 |
| Physiological saline | | 0.84 ± 0.11 | 20.21 ± 1.79 | — |
| Indomethacin | 0.5 | 0.77 ± 0.10 | 6.13 ± 1.64 *3 | 69.7 | test *1: P < 0.05 *2: P < 0.01 *3: P < 0.001

TABLE 8

| | Formula | pH | Appearance | Residue (%) |
|---|---|---|---|---|
| 1 Week | A-1 | pH 6.0 | + | 38.6 |
| | -2 | pH 7.0 | + | 79.3 |
| | -3 | pH 8.0 | — | 100.5 |
| | -4 | pH 9.0 | — | 101.1 |
| 2 Weeks | A-1 | pH 6.0 | + | 23.9 |
| | -2 | pH 7.0 | + | 63.7 |

TABLE 8-continued

| | Formula | pH | Appearance | Residue (%) |
|---|---|---|---|---|
| | -3 | pH 8.0 | — | 98.6 |
| | -4 | pH 9.0 | — | 99.4 |
| 3 Weeks | A-1 | ph 6.0 | + | 19.3 |
| | -2 | pH 7.0 | + | 54.2 |
| | -3 | pH 8.0 | — | 98.0 |
| | -4 | pH 9.0 | — | 99.0 |

Note: The symbol "—" denotes that change in appearance was not observed. The symbol "+" denotes that change in appearance was observed. (hereinafter, the same as above)

TABLE 9

| Formula | 1 Week | 2 Weeks | 4 Weeks |
|---|---|---|---|
| B-1 | — | — | — |
| B-2 | — | — | + |

TABLE 10

| Formula | Residue (%) | Appearance |
|---|---|---|
| B-1 | 93.4 | + |
| B-3 | 100.9 | — |

TABLE 11

| | Appearance | Residue (%) |
|---|---|---|
| Example 6 | — | 100.9 |
| Example 7 | — | 99.2 |
| Example 8 | — | 98.9 |

What is claimed is:

1. A locally administrable opthalmic, otic or nasal therapeutic composition for the treatment of inflammatory disease of the eye, ear or nasal passage which comprises an anti-inflammatory effective amount of a benzoylphenylacetic acid of the formula

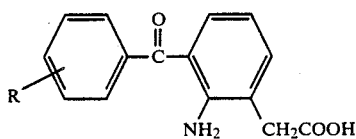

wherein R is hydrogen or a halogen atom or a pharmaceutically acceptable salt thereof or a hydrate of said acid or salt in admixture with
(a) an isotonizing agent, and
(b) at least one member of the group consisting of a microbial agent and a preservative.

2. The locally administrable therapeutic composition for inflammatory disease according to claim 1, wherein the water-soluble polymer is polyvinyl pyrrolidone, polyvinyl alcohol, carboxypropylcellulose, hydroxyethylcellulose, hydroxypropylcellulose or sodium salt of polyacrylic acid.

3. The locally administrable therapeutic composition for inflammatory disease according to claim 1, wherein the concentration of the water-soluble polymer is in the range of about 0.1–10 W/W %.

4. The locally administrable therapeutic composition for inflammatory disease according to claim 1, wherein the sulfite is in the form of sodium, potassium, calcium or magnesium salt.

5. The locally administrable therapeutic composition for inflammatory disease according to claim 1, wherein the concentration of the sulfite is in the range of about 0.1–1 W/W %.

6. A composition according to claim 1 in the form of an aqueous solution.

7. A method of treating animals or humans to alleviate inflammation of the eye, nasal passage or ear canal which comprises applying to the eye, nasal passage or ear canal an anti-inflammatory effective amount of a compound of the formula:

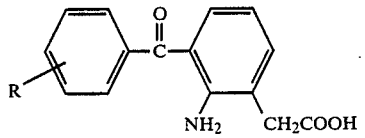

wherein R is hydrogen or a halogen atom or a pharmaceutically acceptable salt thereof, or a hydrate of said acid or salt, as active ingredient.

8. In a locally administrable stable aqueous therapeutic composition for use in the treatment of inflammatory disease comprising an anti-inflammatory effective amount of a benzoylphenylacetic acid of the formula

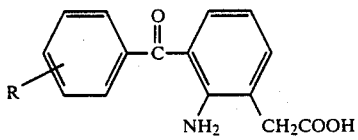

wherein R is hydrogen or a halogen atom, or a pharmaceutically acceptable salt thereof, or a hydrate of said acid or salt, the improvement wherein said composition contains a stabilizing amount of a water-soluble polymer and a sulfite, the pH of said composition being in the range of about 6–9.

9. A locally administrable opthalmic ointment for the treatment of inflammatory disease of the eye which comprises an anti-inflammatory effective amount of a benzoylphenylacetic acid of the formula

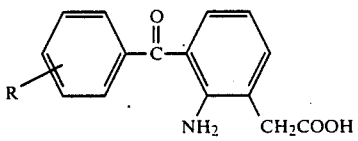

wherein R is hydrogen or a halogen atom or a pharmaceutically acceptable salt thereof or a hydrate of said acid or salt in admixture with an eye ointment base.

* * * * *

UNITED STATES PATENT AND TRADEMARK OFFICE
CERTIFICATE OF CORRECTION

PATENT NO. : 4,910,225

DATED : March 20, 1990

INVENTOR(S) : TAKAHIRO OGAWA ET AL.

It is certified that error appears in the above-identified patent and that said Letters Patent is hereby corrected as shown below:

Column 15, line 19, change "1" to --8--;

line 26, change "1" to --8--;

line 30, change "1" to --8--;

line 35, change "1" to --8--.

Signed and Sealed this

Second Day of March, 1993

Attest:

STEPHEN G. KUNIN

Attesting Officer

Acting Commissioner of Patents and Trademarks